United States Patent [19]

Peers-Trevarton

[11] Patent Number: 4,938,822
[45] Date of Patent: Jul. 3, 1990

[54] METHOD FOR MAKING ASSEMBLY OF PACING LEAD ELECTRODE TO COILED CONDUCTOR

[76] Inventor: C. A. Peers-Trevarton, 739 NW. 83 Dr., Coral Springs, Fla. 33065

[21] Appl. No.: 542,743

[22] Filed: Oct. 17, 1983

[51] Int. Cl.⁵ .............................................. B32B 01/00
[52] U.S. Cl. ...................................... 156/144; 156/293
[58] Field of Search ............... 156/294, 293, 144, 157; 29/451, 854, 881; 267/167; 128/784, 419 P, 786

[56] References Cited

U.S. PATENT DOCUMENTS

| | | | |
|---|---|---|---|
| 1,240,170 | 9/1917 | Block | 267/167 |
| 2,530,163 | 11/1950 | Goodwin | 156/294 X |
| 2,779,647 | 1/1957 | Hamm | 267/167 X |
| 2,822,857 | 2/1958 | Rothermel et al. | 156/144 |
| 4,000,745 | 1/1977 | Goldberg | 128/419 P |
| 4,236,525 | 12/1980 | Sluetz et al. | 128/419 P |
| 4,402,330 | 9/1983 | Lindemans | 128/786 |
| 4,437,474 | 3/1984 | Peers-Treyarton | 128/784 |
| 4,469,104 | 9/1984 | Peers-Trevarton | 128/786 X |
| 4,506,680 | 3/1985 | Stokes | 128/419 P X |
| 4,564,023 | 1/1986 | Hess | 128/419 P X |

FOREIGN PATENT DOCUMENTS 0553327  5/1923  France .
0612831 11/1948  United Kingdom ............... 267/167

Primary Examiner—Raymond Hoch
Attorney, Agent, or Firm—Lockwood, Alex, Fitzgibbon & Cummings

[57] ABSTRACT

Electrode assemblies are provided such that a wire coil conductor is springingly secured into a tubular electrode or onto a pin without having to crimp, stake, weld, swage, or otherwise mechanically secure the wire coil electrode to the tubular electrode or pin. A simple assembly having high separation forces is provided by utilizing a wire coil electrode that, when untensioned, is either oversized with respect to the tubular electrode or is undersized with respect to the pin. Either the oversized wire coil electrode is rotated into the tubular electrode while reducing its oversized condition and placing same into a tensioned condition in order to secure it within the tubular electrode, or the undersized wire coil is rotated onto the pin in order to increase its undersized condition and simultaneously impart a tensioned condition thereto in order to springingly engage the wire coil electrode onto the pin. Enhanced securement is achieved when an adhesive is applied to the interface between the wire coil electrode and the tubular electrode or pin prior to assembly.

2 Claims, 1 Drawing Sheet

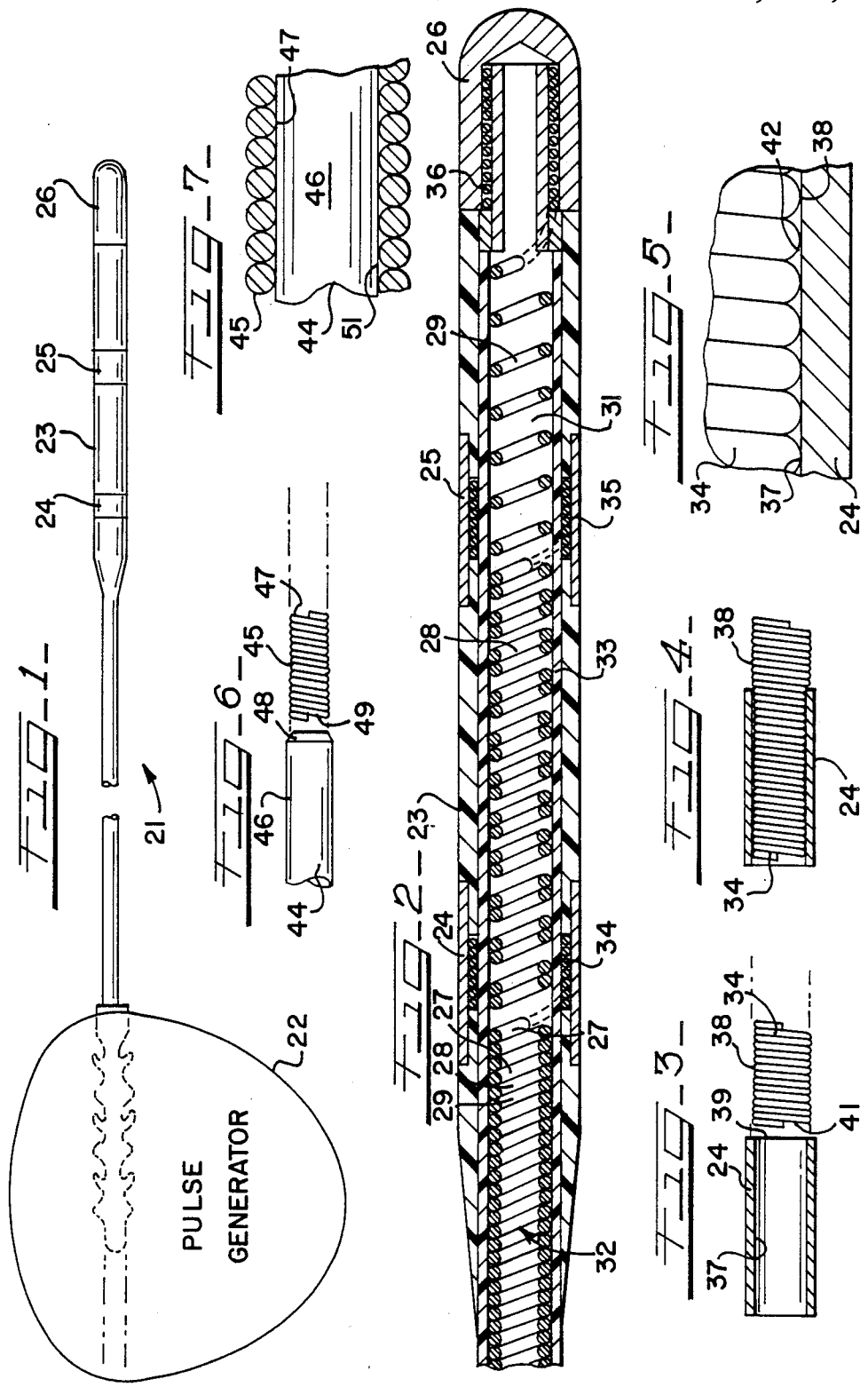

METHOD FOR MAKING ASSEMBLY OF PACING LEAD ELECTRODE TO COILED CONDUCTOR

DESCRIPTION

This invention generally relates to electrode assemblies, and more particularly to a method for securing a wire coil electrode into a tubular electrode or onto a pin and electrode assemblies produced thereby. These electrode assemblies are characterized by including coil-shaped electrodes that have an oversized untensioned condition prior to insertion into a tubular electrode or that have an undersized untensioned condition prior to insertion onto a pin. In either case, such insertion includes radially rotating the coil-shaped conductor and the sleeve or pin with respect to each other while permitting their longitudinal movement to form the electrode assembly.

There are many instances where precise and secure assembly is required along a longitudinally extending interface, including a generally cylindrical interface, between electrical components. When it is of great importance to have the assembly withstand high separation forces when in use, for example when included within a pacer assembly for implantation within humans, it has been typical in the past to utilize assembly procedures that require mechanical fixtures, tooling or devices that include assembly techniques such as crimping, staking, spot welding, swaging, or the like. Such operations tend to be rather complex and require significant capital investment.

These types of assembly methods have been utilized in conjunction with cardiac pacing leads and the like having electrodes that include the assembly of a wire coil electrode to a longitudinally extending electrode such as a sleeve electrode, tip electrode or pin. Such devices provide an opportunity for utilization of the present invention in order to enhance the reliability required for such devices that must provide long-lasting and consistent transmission of electrical signals from a pulse generator, or pacer, to an electrode near the distal end of the device in order that the electrical signals will be imparted to a pre-selected region on the wall of the heart. Often such devices include pacing leads having multiple electrodes for applying stimulating pulses to the atrial or ventricular chamber of the heart.

It is very important that devices of this type be very compact in structure and have a minimum diameter so as to minimize any likelihood of trauma when the device is inserted into the patient. Utilizing the coiled wire conductor is extremely useful in meeting this objective, and in meeting this objective it is extremely important that such be accomplished in a manner in which the wire coil electrode is reliably and firmly attached to its sleeve electrode or pin so as to minimize the possibility of variations in the mechanical engagement between the wire coil and the sleeve electrode or pin. Such is important in order to minimize the possibility of inconsistent electrical properties caused by variations across the engagement interface even when the device is flexed.

The present invention provides this type of enhanced reliability by providing a coil-shaped electrode that has an untensioned oversized condition prior to its insertion into a tubular electrode or the like, which coil-shaped electrode is force-screwed into the tubular electrode in a manner that reduces the size of the outside perimeter of the coil-shaped electrode to an inserted size that is under tension and that is substantially the same size as that of the interior of the tubular electrode. This invention also includes assemblies of an undersized coil-shaped electrode onto a pin.

It is accordingly a general object of the present invention to provide an improved electrode assembly.

Another object of this invention is to provide an improved electrode assembly that is especially reliable and secure, while still being flexible, and which is assembled by techniques that are extremely simple and withstand high separation forces.

Another object of this invention is to provide an improved electrode assembly and method for making same that avoids the use of mechanical complexities such as crimping, staking, spot welding, swaging or the like.

Another object of the present invention is to provide an improved electrode assembly device and method that utilizes a coil-shaped electrode having an undersized or oversized untensioned condition.

These and other objects of the present invention will become apparent from the following detailed description of this invention, taken in conjunction with the accompanying drawings, wherein:

FIG. 1 is an elevational view of a typical device that is suitable for use in connection with this invention, such device being a pacing lead assembly and a pulse generator therefor;

FIG. 2 is an enlarged longitudinal sectional view of the distal end of the device illustrated in FIG. 1;

FIG. 3 is partially sectioned detail view illustrating the preassembly condition of a tubular electrode assembly in accordance with this invention;

FIG. 4 is a view similar to FIG. 3 after partial insertion of the coil-shaped electrode into the tubular electrode;

FIG. 5 is an enlarged detail partial sectional view illustrating an adhesive-supplemented assembly interface for the electrode assembly according to this invention as it is generally illustrated in FIGS. 2 and 4;

FIG. 6 is an elevational view illustrating a preassembly condition of the electrode assembly according to this invention wherein the assembly includes a coil-shaped electrode and a pin; and FIG. 7 is an enlarged detail partial sectional view of the assembly illustrated in FIG. 6 in its assembled condition and further including an adhesive-enhanced assembly feature.

A device of the type generally shown in FIGS. 1 and 2 illustrates the type of environment within which the present invention is utilized, while FIG. 2 also illustrates a typical structure for an electrode assembly according to this invention that is associated with a conductor member for electrical communication to another component of the overall device.

More particularly, FIG. 1 illustrates a cardiac pacing device, generally designated as 21, that includes a pulse generator of generally known construction, schematically illustrated at 22, as well as a pacing lead 23. Illustrated pacing lead 23 is multipolar in that it includes a plurality of generally tubular or sleeve electrodes 24, 25 and 26. Electrode 26 can also be considered as a tip electrode. Each tubular electrode 24, 25, 26 is connected to a conductor 27, 28, 29, respectively Preferably, each of conductors 27, 28, 29 is coiled within a longitudinal bore 31 within the pacing lead 23. While within the bore 31, the conductors 27, 28, 29 are insulated from each other and are wound with each other so as to form a single coil, generally designated at 32.

Conductor 27 passes through an insulating sheath 33 to form an uninsulated coil-shaped electrode 34 that is in electrical contact with the tubular or sleeve electrode 24. Similarly, the conductor 28 passes through the insulating sheath 34 to form an uninsulated coil-shaped electrode 35 that is in electrical contact with the tubular or sleeve electrode 25, and the conductor 29 passes through the insulating sheath 33 to form an uninsulated coil-shaped electrode 36 that is in electrical contact with the tubular, sleeve or tip electrode 26.

FIGS. 3, 4 and 5 illustrate in more detail the electrical contact relationship between the tubular electrodes 24, 25, 26 and the coil-shaped electrodes 34, 35, 36, respectively. For convenience, reference is made to only the sleeve electrode 24 and the coil-shaped electrode 34. When in its untensioned condition as illustrated in FIG. 3, the coil-shaped electrode 34 has an average circumference that is oversized with respect to the inside, generally cylindrical surface 37 of the tubular or sleeve electrode 24. The outer surface of the coil-shaped electrode 34 is a generally helically-shaped surface 38.

At the position illustrated in FIG. 3, the sleeve electrode 24 and the coil-shaped electrode 34 are generally coaxially aligned with each other to the extent that their respective free ends 39, 41 are positioned for contacting each other. Free end 39 and free end 41 are then brought into engagement with each other and either or both of the sleeve electrode 24 and/or the coil-shaped electrode 34 are radially rotated with respect to each other generally along their coaxis. Such radial rotation is in the direction whereby the combination of radial rotation and engagement between the free end 39 and the inside surface 37 of the sleeve electrode 24 will cause the free end 41 of the coil-shaped electrode 34 to decrease in circumferential size to a size that is generally the same as the circumference of the inside surface 37. Continued radial rotation in this manner, while simultaneously permitting longitudinal movement of the coil-shaped electrode 34 with respect to the sleeve electrode 24 generally along their coaxis, results in an increase in the length of the engagement between the helically-shaped surface 38 and the inside surface 37 until such time as the desired amount of the coil-shaped electrode 34 has entered into the sleeve electrode 24.

By this procedure, the coil-shaped electrode 34 is put under tension by the smaller-circumferenced inside surface 37 of the sleeve electrode 24, thereby springingly securing the coil-shaped electrode 34 within the sleeve electrode 24. By virtue of this force screwing of the coil-shaped electrode into the sleeve electrode 24, the spiral surface 38 of the coil-shaped electrode 34 is springingly urged firmly against the inside surface 37 of the sleeve electrode 24.

When it is desired to further enhance the security of the electrical contact engagement between the sleeve electrode 24 and the coil-shaped electrode 34, the helical surface 38 at the free end 41 of the coil-shaped electrode 34 can be coated with an adhesive prior to the radial rotation which force screws the coil-shaped electrode 34 into the sleeve electrode 24. As the radial rotation proceeds in the presence of the adhesive, the intersticies between the helical surface 38 will be filled with the adhesive which will then come into contact with and, when set, adhere to the inside surface 37 of the sleeve electrode 24.

Because of the springingly biased interference fit between the helically-shaped surface 38 and the inside surface 37, the adhesive is automatically wiped from the helically-shaped surface 38. In this manner, the set adhesive does not interfere with the electrical contact between the helically-shaped surface 38 of the coil-shaped electrode 34 and the inside surface 37 of the sleeve electrode 24. When the adhesive has set, adhesive threads 42 are formed on the inside surface 37 at the intersticies between the helically-shaped surface 38. Adhesive threads 42 are in the form of a raised spiral ridge.

When the adhesive threads 42 are formed as described, the coil-shaped electrode 34 is secured in place within the sleeve electrode 24 in three distinct ways. There is a mechanical interference fit between the inside surface 37 and the helically-shaped surface 38 by virtue of the springing engagement caused by the oversized untensioned condition of the coil-shaped electrode 34. The set adhesive is chemically adhered to both the intersticies of the coil-shaped electrode 34 and to the inside surface 37 of the sleeve electrode 24. Adhesive threads 42 threadingly engage the coil-shaped electrode 34 into the sleeve electrode 24.

Another embodiment of the invention is illustrated in FIGS. 6 and 7 wherein a pin 44, which may also be an electrode, is secured to a coil-shaped electrode 45 which, prior to assembly, has an undersized untensioned condition. More particularly, the pin 44 has an outside surface 46 having a predetermined circumference, whereas the coil-shaped electrode 45 has a helically-shaped inner surface 47 having an average circumference that is less than the circumference of the outside surface 46 of the pin 44.

Force screwing of the coil-shaped electrode 45 onto the pin 44 is effected by first generally coaxially aligning the pin 44 and the coil-shaped electrode 45 and positioning their respective free ends 48, 49 generally adjacent to each other. Free ends 48, 49 are radially rotated with respect to each other and are brought into engagement with each other. This radial rotation is in a direction such that the radial rotation in combination with the engagement between the free end 48 of the pin 44 and the free end portion of the helically-shaped inner surface 47 increases the diameter of the helically-shaped inner surface at such free end 49. This process may be facilitated by including a chamfer at the free end 48 as illustrated. Radial rotation is continued, while permitting longitudinal movement of the coil-shaped electrode 45 with respect to the pin until such time as the desired length of the coil-shaped electrode 45 is inserted onto the pin 44. When rotation is completed, the coil-shaped electrode 45 is springingly urged onto the pin 44 in a uniform and secure manner.

When desired, enhanced securement can be provided by forming an adhesive thread 51 at the intersticies between the helically-shaped inner surface 47. An adhesive is deposited on the helically-shaped inner surface 47 at the free end 49 of the coil-shaped electrode 45 before the radial rotation step, which radial rotation step wipes the adhesive from the helically-shaped inner surface 47 and forms the raised spiral ridge that is the adhesive thread 51.

Numerous other embodiments of this invention will be apparent to those skilled in the art, especially with respect to the environment within which the electrode assemblies are included, without departing from the spirit and scope of this invention. Therefore, this invention is to be defined only by the appended claims.

I claim:

1. A method of manufacturing a pacing lead electrode assembly that includes a coiled conductor within a sleeve electrode having a generally cylindrical inside surface, comprising:

selecting an electrically conductive metal sleeve electrode having an electrically conductive generally cylindrical inside surface of a predetermined circumference;

oversizing an electrically conductive coiled conductor in its generally radial cross-section so as to provide a coil-shaped conductor member having a generally helically shaped uninsulated electrically conductive outer surface that is radially oversized with respect to the electrically conductive inside surface circumference of the sleeve electrode to the extent that the helically shaped outer surface has a average circumference that is greater than the circumference of the generally cylindrical inside surface of the sleeve electrode when the coil-shaped conductor is in a radially untensioned preassembly condition;

applying adhesive to a free end of the oversized coil-shaped conductor member;

generally coaxially aligning the free end of the oversized coil-shaped conductor member with a free end of the sleeve electrode;

radially rotating the oversized coil-shaped conductor member or the sleeve electrode with respect to each other generally along their coaxis;

engaging the oversized coil-shaped conductor free end and the sleeve electrode free end during said radial rotation step to thereby flow said adhesive to intersticies between said generally helically shaped outer surface and to thereby radially decrease the oversized circumference of the free end of the coil-shaped conductor member to the extent that the free end of the coil-shaped conductor member rotates into the free end of the sleeve electrode and is radially tensioned thereby;

continuing said radial rotation step while permitting longitudinal movement of the coil-shaped conductor member with respect to the sleeve electrode generally along their coaxis, whereby the coil-shaped conductor member moves longitudinally into the sleeve electrode to form an electrode assembly having a plurality of windings of the coiled conductor radially tensioned and springingly urged against and engaged with the electrically conductive generally cylindrical inside surface of the sleeve electrode to enhance electrical contact between the electrically conductive outer surface of the coiled conductor and the electrically generally cylindrical inside surface of the sleeve electrode; and setting the adhesive in the intersticies to form an adhesive thread onto said inside surface of the sleeve electrode.

2. A method of manufacturing a pacing lead electrode assembly that includes a coiled conductor mounted onto a pin electrode having a generally cylindrical outside surface comprising:

selecting an electrically conductive metal pin electrode having an electrically conductive generally cylindrical and substantially unthreaded outside surface of a predetermined circumference;

undersizing an electrically conductive coiled conductor in its generally radial cross-section so as to provide a coil-shaped conductor member having a generally helically shaped uninsulated electrically conductive inner surface that is radially undersized with respect to the electrically conductive substantially unthreaded outside surface of the pin electrode to the extent that the helically shaped inner surface has an average circumference that is less than the circumference of the generally cylindrical outside surface of the sleeve electrode when the coil-shaped conductor member is in a radially untensioned preassembly condition;

applying adhesive to a free end of the undersized coil-shaped conductor member;

generally coaxially aligning a free end of the undersized coil-shaped conductor member with a free end of the pin electrode;

radially rotating the undersized coil-shaped conductor member or the pin electrode with respect to each other generally along their coaxis;

engaging the undersized coil-shaped conductor free end and the pin electrode free end during said radial rotation step to thereby flow said adhesive to intersticies between said generally helically shaped inner surface and to thereby radially increase the undersized circumferenece of the free end of the coil-shaped conductor member to the extent that the free end of the coil-shaped conductor member rotates onto the free end of the pin electrode and is radially tensioned thereby;

continuing said radial rotation step while permitting longitudinal movement of the coil-shaped conductor member with respect to the pin electrode generally along their coaxis, whereby the coil-shaped conductor member moves longitudinally onto the pin electrode to form an assembly having a plurality of windings of the coil-shaped conductor radially tensioned and springingly urged against and engaged with the electrically conductive, generally cylindrical outside surface of the pin electrode to enhance the electrical contact between the electrically conductive inner surface of the coiled conductor and the electrically conductive cylindrical outside surface of the pin electrode; and setting the adhesive in the intersticies to form an adhesive thread onto said outside surface of the pin.

* * * * *